(12) United States Patent
Qi et al.

(10) Patent No.: US 12,324,871 B2
(45) Date of Patent: Jun. 10, 2025

(54) ABSORBABLE IRON-BASED ALLOY IMPLANTED MEDICAL DEVICE AND MANUFACTURING METHOD THEREOF

(71) Applicant: Lifetech Scientific (Shenzhen) Co., Ltd., Shenzhen (CN)

(72) Inventors: Haiping Qi, Shenzhen (CN); Wenjiao Lin, Shenzhen (CN)

(73) Assignee: BIOTYX MEDICAL (SHENZHEN) CO., LTD., Shenzhen (CN)

( * ) Notice: Subject to any disclaimer, the term of this patent is extended or adjusted under 35 U.S.C. 154(b) by 788 days.

(21) Appl. No.: 15/776,514

(22) PCT Filed: Jun. 8, 2016

(86) PCT No.: PCT/CN2016/085187
§ 371 (c)(1),
(2) Date: May 16, 2018

(87) PCT Pub. No.: WO2017/084314
PCT Pub. Date: May 26, 2017

(65) Prior Publication Data
US 2018/0326128 A1 Nov. 15, 2018

(30) Foreign Application Priority Data
Nov. 18, 2015 (CN) .......................... 201510799593.7

(51) Int. Cl.
*A61L 31/02* (2006.01)
*A61F 2/82* (2013.01)
(Continued)

(52) U.S. Cl.
CPC .............. *A61L 31/148* (2013.01); *A61F 2/82* (2013.01); *A61L 27/04* (2013.01); *A61L 31/022* (2013.01);
(Continued)

(58) Field of Classification Search
CPC ................ A61F 2/82; A61F 2210/0004; A61F 2210/0076; A61F 2/28; A61F 2310/00017;
(Continued)

(56) References Cited

U.S. PATENT DOCUMENTS 5,605,696 A * 2/1997 Eury ........................ A61L 31/10
424/423
9,333,099 B2 * 5/2016 Pacetti ...................... A61F 2/82
(Continued)

FOREIGN PATENT DOCUMENTS

AU 2014200856 A1 * 3/2014 ............... A61F 2/02
CN 101411892 A 4/2009
(Continued)

OTHER PUBLICATIONS

Mohd Daud et al. ("Degradation and in vitro cell-material interaction studies on hydroxyapatitecoated biodegradable porous iron for hard tissue scaffolds", Journal of Orthopaedic Translation, 2014, 2, 177-184).*
(Continued)

*Primary Examiner* — Brian E Pellegrino
(74) *Attorney, Agent, or Firm* — Raymond Sun (57) ABSTRACT

Disclosed are an absorbable iron-based alloy implanted medical device (1) and preparation method thereof. The device (1) comprises an iron-based alloy base (11), a degradable polymer (13) arranged on the surface of the iron-based alloy base, and an alkaline protector (12) arranged on the surface of the iron-based alloy base. The alkaline protector (12) contains at least one alkaline substance capable of neutralizing the acidic substance produced by the polymer at the early stage after the device is implanted to delay the corrosion of the iron-based alloy base (1) in the early stage of implantation, hence the iron-based alloy base (12) would
(Continued)

not substantially corrode or would corrode slowly, clinically satisfying the mechanical properties and requirements of the device (1) in the early stage of implantation; and in the meantime, after the neutralization and consumption of the alkaline protector (12) exposes the base (11), the base (11) can still accelerate the corrosion speed thereof in the acidic environment formed by the polymer (13), so as to clinically satisfy the requirement of the corrosion cycle of the device (1) at the same time.

14 Claims, 1 Drawing Sheet

(51) Int. Cl.
*A61L 27/04* (2006.01)
*A61L 31/10* (2006.01)
*A61L 31/14* (2006.01)

(52) U.S. Cl.
CPC ....... *A61L 31/10* (2013.01); *A61F 2210/0004* (2013.01); *A61F 2210/0076* (2013.01); *A61F 2250/0067* (2013.01); *A61L 2400/18* (2013.01)

(58) Field of Classification Search
CPC .. A61L 31/022; A61L 2400/18; A61L 31/086; A61L 31/148; A61L 2420/08; A61L 31/10; A61L 31/143; A61L 31/127; A61L 27/28; A61L 31/08; C23C 16/407; C23C 8/18
See application file for complete search history.

(56) References Cited

U.S. PATENT DOCUMENTS

| | | | |
|---|---|---|---|
| 2003/0180371 A1 | 9/2003 | Reslow et al. | |
| 2005/0100578 A1* | 5/2005 | Schmid | A61F 2/28 623/16.11 |
| 2005/0149173 A1* | 7/2005 | Hunter | A61L 31/16 623/1.42 |
| 2008/0057105 A1* | 3/2008 | Atanasoska | A61L 27/28 514/44 R |
| 2008/0147177 A1* | 6/2008 | Scheuermann | A61F 2/06 623/1.42 |
| 2008/0183278 A1* | 7/2008 | Atanasoska | A61L 31/16 623/1.17 |
| 2010/0222873 A1* | 9/2010 | Atanasoska | A61L 31/148 623/1.42 |
| 2011/0276124 A1* | 11/2011 | Doerr | A61L 31/022 623/1.15 |
| 2016/0262915 A1* | 9/2016 | Mangiardi | A61L 31/088 |
| 2017/0106123 A1* | 4/2017 | Weber | A61L 31/148 623/1.46 |

FOREIGN PATENT DOCUMENTS

| | | | | |
|---|---|---|---|---|
| CN | 101560686 A | | 10/2009 | |
| CN | 103096945 A | * | 5/2013 | ........... A61L 31/148 |
| CN | 103418035 A | | 12/2013 | |
| CN | 103889474 A | | 6/2014 | |
| CN | 104587534 A | | 5/2015 | |
| CN | 104857570 A | | 8/2015 | |
| WO | WO-9741273 A1 | * | 11/1997 | ............. A61L 27/32 |
| WO | 2014165652 A1 | | 10/2014 | |
| WO | WO-2015046388 A1 | * | 4/2015 | ............. A61L 27/54 |

OTHER PUBLICATIONS

Dingeldein, CN 103096945 translation (Year: 2013).*
Takeuchi, WO 2015046388 translation (Year: 2015).*
Second Office Action for corresponding China Application No. 201510799593.7.
Office Action dated Jan. 30, 2019 for corresponding China Application No. 201510799593.7.
International Search Report dated Aug. 2, 2016 for corresponding PCT Application No. PCT/CN2016/085187.
Supplementary European search report dated Jun. 19, 2021 of corresponding Europe application No. 16865495.2.
Office action dated Jan. 30, 2019 of corresponding Chinese application No. 201510799593.7.

* cited by examiner

ABSORBABLE IRON-BASED ALLOY IMPLANTED MEDICAL DEVICE AND MANUFACTURING METHOD THEREOF

TECHNICAL FIELD

The present application relates to the field of medical devices, and more particularly relates to an absorbable iron-based alloy implanted medical device and a manufacturing method thereof.

BACKGROUND ART

At present, the most frequently applied materials for an absorbable implanted medical device substrate include polymers, a magnesium-based alloy and an iron-based alloy, and the most frequently applied polymer is polylactic acid, which can be completely degraded and absorbed, with degradation products of carbon dioxide and water, but its mechanical property is poor. The size of the polymer-based device should be larger than the metal-based device so that the polymer-based device has the same mechanical property as the metal-based device, which limits application of the polymer-based device. The magnesium-based alloy and the iron-based alloy have advantages of convenience in processing and molding and high mechanical strength. However, as the magnesium-based alloy corrodes too quickly in a human body and the accompanying corrosion may produce hydrogen, it is necessary to enlarge the size of a magnesium-based alloy device to obtain the mechanical property in the early stage of implantation, and in this way, the application of the magnesium-based alloy device is limited as well.

In terms of clinical application, when the absorbable implanted medical device fulfills its expected use, after a diseased portion is cured and has recovered to its normal shape and function (cured), so as to not cause a new biological compatibility problem, it is desirable for the device to completely corroded or degraded, and absorbed by an organ, as quickly as possible. According to different portions to which the device is clinically applied, the recovery period is generally considered as 1 to 6 months, and within this period of time, the device is required to keep a structural integrality and have a sufficient mechanical property. The iron-based alloy has a good biological compatibility. but due to the slow corrosion of the iron-based alloy in the body, an iron-based alloy device would require a long time to be completely corroded after the diseased portion is cured; and therefore, it is necessary to accelerate corrosion to shorten the corrosion cycle of the iron-based alloy device.

A research has shown that if the surface of the iron-based alloy is coated with a degradable polyester coating, its corrosion speed would be increased. Degradation of the degradable polyester coating in the body would lower the pH value of a local microenvironment near a device implantation position, thereby forming a local micro acidic environment where the iron-based alloy is corroded faster to generate iron salt and/or iron oxides and/or iron hydroxides serving as corrosion products.

For the iron-based alloy device of a predetermined specification, the corrosion speed of the iron-based alloy, and whether the iron-based alloy is finally completely corroded or not, are determined according to the amount of the degradable polyester coating and the type and the nature of degradable polyester. Under conditions that the type and the nature of the degradable polyester have been selected and the amount of the degradable polyester is sufficient to completely corrode an iron-based alloy substrate have been determined, excessively high corrosion speed or local severe corrosion of the iron-based alloy would affect the structural integrality and the mechanical property of the iron-based alloy device in the early stage of implantation (1 to 6 months, namely the above-mentioned recovery period), therefore it is difficult for the device to meet the requirements for clinical application during the early stage of implantation. These defects are specifically as follows: (1) a degradation product of the degradable polyester coating is acidic, and there are small molecular residues with a higher degradation speed in degradable polyester (for example, the standard monomer residue amount of the polylactic acid is less than 2%), that will result in faster corrosion of the iron-based substrate during the early stage of implantation; for example, after the device is implanted into a coronary artery for about 1 to 7 days, excessively fast corrosion and accumulation of the corrosion products cause incomplete endothelialization of the inner surface of the device, which increases the risk of acute thrombosis and subacute thrombosis; and (2) the heterogeneity of degradable polyester degradation easily leads to non-uniform corrosion of the iron-based alloy substrate, and local fast corrosion possibly results in breakage, so that the iron-based alloy substrate is unable to meet the requirements of structural integrity and a requisite mechanical property during the early stage. Although the excessively fast corrosion of the iron-based alloy device during the early stage of implantation can be prevented by reducing the amount of the degradable polyester coating, the corrosion cycle of the iron-based alloy device would be prolonged. Therefore, for an iron-based alloy device that includes the degradable polyester, under the conditions that the type and the nature of the degradable polyester and the amount ratio of the degradable polyester to the iron-based alloy have been determined, it is necessary to seek a way to reduce the early corrosion speed of the iron-based substrate in the acidic environment formed by the degradable polyester to guarantee the mechanical property of the device during the early stage of implantation.

SUMMARY OF THE INVENTION

The object of the present application is to provide an absorbable iron-based alloy implanted medical device and a manufacturing method thereof. After being implanted into a body, at least part of the device is corroded slowly or is not totally corroded within 1 to 6 months, and can meet the clinical requirement on a mechanical property of the device during the early stage of implantation within this period of time.

An absorbable iron-based alloy implanted medical device is provided, including: an iron-based alloy substrate and a degradable polymer disposed on the surface of the iron-based alloy substrate, and further including an alkaline protector disposed on the surface of the iron-based alloy substrate.

According to the absorbable iron-based alloy implanted medical device of an embodiment of the present application, the alkaline protector may cover the entire surface of the iron-based alloy substrate, and the degradable polymer covers at least part of the surface of the alkaline protector.

According to the absorbable iron-based alloy implanted medical device of an embodiment of the present application, the alkaline protector may cover part of the surface of the iron-based alloy substrate, and the degradable polymer covers at least part of the surface of the alkaline protector and/or covers at least part of the surface of a region of the iron-based alloy substrate, which is not covered by the alkaline protector.

According to the absorbable iron-based alloy implanted medical device of the embodiments of the present application, the alkaline protector includes at least one alkaline substance. The alkaline substance is selected from the group consisting of sodium hydroxide, potassium hydroxide, magnesium hydroxide, zinc hydroxide, magnesium oxide, zinc oxide, sodium carbonate, sodium bicarbonate, potassium carbonate, potassium bicarbonate, calcium carbonate, sodium phosphate, sodium hydrogen phosphate, potassium phosphate, potassium hydrogen phosphate, calcium phosphate, calcium hydrogen phosphate, sodium pyrophosphate, trisodium monohydrogen diphosphate, potassium pyrophosphate, tripotassium monohydrogen diphosphate, calcium pyrophosphate, calcium hydrogen diphosphate, sodium polyphosphate, potassium polyphosphate, calcium polyphosphate, ammonium polyphosphate, hydroxyapatite, carbonated hydroxyapatite, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium, ethylene diamine tetraacetic acid tetrapotassium, ethylene diamine tetraacetic acid calcium, sodium ethoxide, potassium ethoxide, calcium ethoxide, urea and hexamine.

According to the absorbable iron-based alloy implanted medical device of the embodiments of the present application, the alkaline protector includes at least one alkaline substance. The alkaline substance includes weak acid and strong alkali salt which is selected from the group consisting of sodium carbonate, sodium bicarbonate, potassium carbonate, potassium bicarbonate, sodium phosphate, sodium hydrogen phosphate, potassium phosphate, potassium hydrogen phosphate, calcium phosphate, calcium hydrogen phosphate, sodium pyrophosphate, trisodium monohydrogen diphosphate, potassium pyrophosphate, tripotassium monohydrogen diphosphate, sodium polyphosphate, potassium polyphosphate, calcium polyphosphate, ammonium polyphosphate, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium and ethylene diamine tetraacetic acid tetrapotassium.

According to the absorbable iron-based alloy implanted medical device of the embodiments of the present application, the alkaline protector further includes a slow release assisted substance for prolonging the release time of the alkaline substance. The slow release assisted substance includes a thickener; the thickener is mixed with the at least one alkaline substance to form a mixture; and the volume percentage of the alkaline substance in the mixture is greater than or equal to 20 percent but less than 100 percent; or the slow release assisted substance includes a hydrophobic substance which covers the surface of the alkaline substance to form a hydrophobic layer.

According to the absorbable iron-based alloy implanted medical device of the embodiments of the present application, the alkaline protector further includes an adhesive. The volume percentage of the adhesive is less than or equal to 80 percent.

According to the absorbable iron-based alloy implanted medical device of the embodiments of the present application, a degradable polymer layer with neutral degradation products is further disposed between the iron-based alloy substrate and the alkaline protector.

According to the absorbable iron-based alloy implanted medical device of the embodiments of the present application, the iron-based alloy substrate is pure iron or an iron-based alloy with a carbon content less than or equal to 2.11 wt %.

According to the absorbable iron-based alloy implanted medical device of the embodiments of the present application, an active drug component is mixed into the degradable polymer. The active drug is selected from the group consisting of taxol, sirolimus and its derivative, cilostazol, heparin, dexamethasone, calcium gluconate, chlortrimeton and cortisone.

According to the absorbable iron-based alloy implanted medical device of the embodiments of the present application, the degradable polymer is selected from degradable polyester and/or degradable polyanhydride. The degradable polyester is selected from the group consisting of polylactic acid, polyglycolic acid, polylactic acid-glycolic acid), polycaprolactone, polyhydroxyalkanoate, polyacrylate, poly (ethylene succinate), poly($\beta$-hydroxybutyrate) and polyethylene glycol adipate, or is selected from the group consisting of a physical blend of at least two of the polylactic acid, the polyglycolic acid, the poly(ethylene succinate), the poly($\beta$-hydroxybutyrate), the polycaprolactone, the polyethylene glycol adipate, a polylactic acid-glycollic acid copolymer and a polyhydroxybutyrate-pentanoate copolymer, or is selected from the group consisting of copolymers formed by copolymerizing at least two of monomers forming the polylactic acid, the polyglycolic acid, the poly(ethylene succinate), the poly($\beta$-hydroxybutyrate), the polycaprolactone, the polyethylene glycol adipate, the polylactic acid-glycollic acid copolymer and the polyhydroxybutyrate-pentanoate copolymer. The degradable polyanhydride is selected from the group consisting of poly1,3-bis(p-carboxyphenoxy)propane-sebacic acid, poly(erucic acid dimer-sebacic acid) or poly(fumaric acid-sebacic acid), or the degradable polymer is a copolymer formed by copolymerizing at least two of monomers forming the degradable polyester and the degradable polyanhydride.

The present application further provides a manufacturing method for an absorbable iron-based alloy implanted medical device, including the steps of: covering at least one part of the surface of an iron-based alloy substrate with an alkaline protector, and covering the iron-based alloy substrate and/or the alkaline protector with a degradable polymer.

According to the manufacturing method of the absorbable iron-based alloy implanted medical device of embodiments of the present application, the step of covering the surface of the iron-based alloy substrate with the alkaline protector includes: covering the surface of the iron-based alloysubstrate with an alkaline substance via spray coating, dip coating, brush coating, 3D printing, electrostatic spinning or embedding, thereby forming the alkaline protector.

Compared with the prior art, the absorbable iron-based alloy implanted medical device provided by the present application includes the alkaline protector. On one hand, the alkaline protector may neutralize acidic products produced by degradation of the polymer; and on the other hand, the alkaline protector may be used as a spacer configured to isolate the iron-based alloy substrate from a human body environment and isolate the iron-based alloy substrate from a micro acidic environment formed by the degradation of the polymer at the beginning of implantation to relieve early corrosion of the iron-based alloy substrate, so that the device may maintain its mechanical property in the initial stage of implantation. With consumption of the alkaline protector by neutralizing, the exposed iron-based alloy substrate can still be quickly corroded in the micro acidic environment formed by the degradation of the degradable polymer layer, thereby meeting a requirement of a degradation period of the device.

BRIEF DESCRIPTION OF THE DRAWINGS

A detailed description is made to the present application in combination with accompanying drawings and embodiments as follows. In the drawings.

DETAILED DESCRIPTION OF THE INVENTION

An absorbable iron-based alloy implanted medical device is provided, including a lumen stent, a gynecological implant, an andrological implant, a respiratory implant or an orthopedic implant. In order to provide clearer understandings of technical features, objectives and effects of the present application, the lumen stent is taken as an example. Specific implementation modes of the present application are described in detail with reference to the drawings.

The absorbable iron-based alloy implanted medical device (hereinafter referred to as the device) of the present application includes an iron-based alloy substrate (hereinafter referred to as the substrate), an alkaline protector disposed on the surface of the substrate, and a degradable polymer coating disposed on the surface of the substrate and/or the surface of the alkaline protector. The main idea of the present application is that by the additional arrangement of the alkaline protector on the surface of the iron-based alloy substrate, the alkaline protector is configured to isolate the substrate, and a neutralizing reaction occurs between the alkaline protector and an acidic substance produced by the degradable polymer, thereby slowing down early corrosion of the iron-based alloy substrate to ensure that the absorbable iron-based alloy implanted device has a sufficient mechanical property in the early stage and the corrosion cycle of the iron-based alloy substrate is not prolonged.

The alkaline protector may slow down the corrosion of the iron-based alloy substrate during the early stage of implantation. In the protection period of the alkaline protector, the iron-based alloy substrate is corroded slowly, and its mechanical property is rarely reduced, so that with a properly decreased design size, the absorbable iron-based alloy implanted medical device of the present application may also guarantee a mechanical property requirement in the early stage of implantation. Therefore, compared with the prior art, the absorbable iron-based alloy implanted medical device of the present application has a decreased design size, which correspondingly decreases the amount of iron-based alloy and reduces corrosion products of the iron-based alloy.

Figure 1:
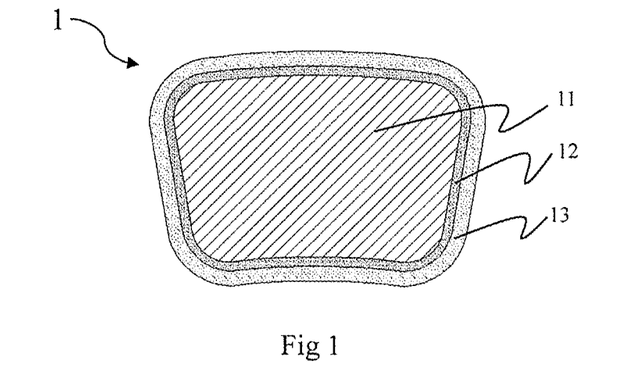
FIG. 1 is a sectional schematic diagram of an absorbable iron-based alloy implanted medical device provided by one embodiment of the present application along a direction perpendicular to its lengthwise direction, wherein an alkaline protector completely covers the whole surface of an iron-based alloy substrate.

With reference to FIG. 1, an absorbable iron-based alloy implanted medical device 1 of the present application includes an iron-based alloy substrate 11, an alkaline protector 12 disposed on the iron-based alloy substrate 11, and a degradable polymer coating 13 disposed on the iron-based alloy substrate 11 and the alkaline protector 12. The alkaline protector 12 may directly cover the surface of the iron-based alloy substrate 11, or they are isolated from each other. For example, a middle layer may be disposed between the iron-based alloy substrate 11 and the alkaline protector 12 to increase an adhesive force of the alkaline protector 12. The absorbable iron-based alloy implanted medical device 1 may be an absorbable lumen stent 1 (hereinafter referred to as the stent 1). The stent 1 may be a blood vessel stent, such as a coronary artery stent or a peripheral stent, which has a radial compression state or a radial expansion state. During use, the stent 1 in the radial compression state is disposed in a delivery device and is delivered to a diseased portion of a lumen through the delivery device, and after being released, it is expanded to the radial expansion state through balloon dilatation to cling to a lumen wall, and is fixed in the lumen through a radial supporting force.

The substrate 11 may be pure iron or an iron-based alloy with a carbon content less than or equal to 2.11 wt. %, such as a product obtained by carburizing and/or nitriding the pure iron.

The degradable polymer layer at least includes one degradable polymer which produces an acidic degradation product, such as carboxylic acid, after being degraded and may be selected from degradable polyester and/or degradable polyanhydride. The degradable polyester is selected from the group consisting of polylactic acid, polyglycolic acid, poly(ethylene succinate), poly(β-hydroxybutyrate), polycaprolactone, polyethylene glycol adipate, a polylactic acid-glycollic acid copolymer and a polyhydroxybutyrate-pentanoate copolymer, or is selected from the group consisting of a physical blend of at least two of the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer, or is selected from the group consisting of a copolymer formed by copolymerizing at least two of monomers forming the polylactic acid, the polyglycolic acid, poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer. The polyanhydride is selected from the group consisting of poly1,3-bis(p-carboxyphenoxy)propane-sebacic acid, poly(erucic acid dimer-sebacic acid) or poly(fumaric acid-sebacic acid); the degradable polyester is selected from the group consisting of the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer; or the degradable polymer includes a blend of the above degradable polyester and the above degradable polyanhydride, or is a degradable copolymer formed by copolymerizing monomers of the above degradable polyester and the above degradable polyanhydride.

When the degradable polymer loads a drug, an active drug component may be further mixed into the degradable polymer layer. An active drug may be a drug for inhibiting vascular proliferation, such as taxol, sirolimus and its derivative, or an antiplatelet drug such as cilostazol, or an antithrombotic drug such as heparin, or an anti-inflammatory reaction drug such as dexamethasone, or an anti-allergen drug such as calcium gluconate, chlortrimeton and cortisone, or a mixture of at least two of the above drugs.

Figure 2:
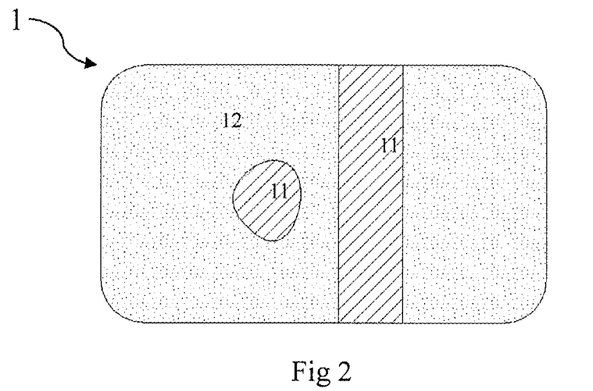
FIG. 2 is a schematic diagram of a degradable polymer layer-removed absorbable iron-based alloy implanted medical device provided by another embodiment of the present application along its lengthwise direction, wherein an alkaline protector covers part of the surface of an iron-based alloy substrate.

There are various positional relationships between the alkaline protector 12 and the iron-based alloy substrate 11. As an implementation mode, as shown in FIG. 1, the alkaline protector 12 directly covers the entire surface of the iron-based alloy substrate 11, and the degradable polymer layer 13 covers at least part of the surface of the alkaline protector 12. In the example as shown in FIG. 1, the degradable polymer layer 13 may further directly cover the entire surface of the alkaline protector 12. As another implementation mode, as shown in FIG. 2 of a surface diagram of a degradable polymer-removed device, the alkaline protector 12 covers part of the surface of the iron-based alloy substrate 11 to expose part of the surface of the iron-based alloy substrate 11. FIG. 1 and FIG. 2 are only used as examples, but not intended to limit the present application. A person skilled in the art can adopt a proper coverage mode as required, for example, the alkaline protector and the degradable polymer may cover the matrix in a staggered manner, but the degradable polymer does not cover the alkaline protector, and no further details are described here.

The absorbable lumen stent 1 further includes the alkaline protector 12 disposed between the substrate 11 and the degradable polymer layer 13. The alkaline protector 12 may include a single alkaline substance, or include a mixture of various single alkaline substances. Or, the alkaline protector 12 may also include a mixture of an alkaline substance and an adhesive. The volume percentage of the alkaline substance in the mixture is greater than or equal to 20 percent but less than 100 percent, that is to say, the volume percentage of the adhesive is less than or equal to 80 percent. The adhesive may be a degradable adhesive or a water-soluble adhesive, for example, it may be at least one of cellulose, lignin, starch, chitin, polyethylene glycol, polyvinyl alcohol, cyclodextrin and water-soluble inorganic salt. Or, the alkaline protector 12 may also include a mixture of the alkaline substance and a thickener. The volume percentage of the alkaline substance in the mixture is greater than or equal to 20 percent but less than 100 percent, and the adhesive may be one or more of gelatin, polyvinylpyrrolidone (PVP) and carboxyl methyl cellulose (CMC). Or, the alkaline protector 12 may also include a mixture of the alkaline substance, the thickener and the adhesive. The volume percentage of the alkaline substance in the mixture is greater than or equal to 20 percent but less than 100 percent, the adhesive provides a better connection between the alkaline substance and the substrate, and the thickener achieves a slow release effect on the alkaline substance, thereby prolonging the non-corrosion time of the substrate.

The alkaline substance included in the alkaline protector 12 may react with hydrogen ions (H<+>), including, but not limited to, sodium hydroxide, potassium hydroxide, magnesium hydroxide, zinc hydroxide, magnesium oxide, zinc oxide, sodium carbonate, sodium bicarbonate, potassium carbonate, potassium bicarbonate, calcium carbonate, sodium phosphate, sodium hydrogen phosphate, potassium phosphate, potassium hydrogen phosphate, calcium phosphate, calcium hydrogen phosphate, sodium pyrophosphate, trisodium monohydrogen diphosphate, potassium pyrophosphate, tripotassium monohydrogen diphosphate, calcium pyrophosphate, calcium hydrogen diphosphate, sodium polyphosphate, potassium polyphosphate, calcium polyphosphate, ammonium polyphosphate, hydroxyapatite, carbonated hydroxyapatite, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium, ethylene diamine tetraacetic acid tetrapotassium, ethylene diamine tetraacetic acid calcium, sodium ethoxide, potassium ethoxide, calcium ethoxide, urea and hexamine, and the alkaline substance is selected from at least one substance listed above.

Weak acid and strong alkali salt in the alkaline substance may achieve a buffer effect in acid-alkali neutralization reaction between the alkaline substance and an acidic environment, making a pH value of the reaction process change slowly[I1]. Specifically, the weak acid and strong alkali salt reacts with the hydrogen ions to produce weak acid. The weak acid and weak acid salt form a buffer solution which may offset or relieve the influence of extra acid or alkali on the pH value of the solution to a certain extent, thereby keeping the pH value of the solution relatively stable. In the present application, the buffer substance may keep the pH value of the region near the degradable polymer (for example the polylactic acid) from experiencing minimal change to a certain extent, and even maintain the pH value near the degradable polymer in a neutral state, so that early degradation of the degradable polymer is slowed down. The weak acid and strong alkali salt may be at least one of sodium carbonate, sodium bicarbonate, potassium carbonate, potassium bicarbonate, sodium phosphate, sodium hydrogen phosphate, potassium phosphate, potassium hydrogen phosphate, calcium phosphate, calcium hydrogen phosphate, sodium pyrophosphate, trisodium monohydrogen diphosphate, potassium pyrophosphate, tripotassium monohydrogen diphosphate, sodium polyphosphate, potassium polyphosphate, calcium polyphosphate, ammonium polyphosphate, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium and ethylene diamine tetraacetic acid tetrapotassium. Therefore, the weak acid and strong alkali salt may be independently used as an alkaline substance and mixed with other alkaline substances, and both of the ways achieve the buffer effect on the acid-alkali neutralization reaction in a process of neutralizing the acidic environment.

The above-mentioned alkaline substance itself (for example, the weak acid and strong alkali salt) is adopted to achieve the buffer effect in the acid-alkali neutralization reaction between the alkaline substance and the acidic environment formed by the degradable polymer; and in addition, the alkaline protector further includes a slow release assisted substance for prolonging the release time of the alkaline substance, such as the above-mentioned thickener. The thickener increases the viscosity of the alkaline protector, thus achieving a slow release effect on the alkaline substance to prolong the non-corrosion time of the substrate; or, a hydrophobic layer may be disposed on the surface of the alkaline substance, and it isolates the alkaline substance to prolong the release time of the alkaline substance. Specifically, the hydrophobic layer may cover the alkaline protector via spray coating, dip coating, brush coating, 3D printing, electrostatic spinning or embedding, and it may reduce contact between the alkaline protector and water (physiological fluid) within a certain time period, thereby prolonging the retention time of the alkaline protector and prolonging the non-corrosion time of the substrate.

The hydrophobic layer includes at least one hydrophobic substance used as the slow release assisted substance which at least includes a hydrophobic group, and the hydrophobic group may be an oily substance and/or an anionic surfactant. The oily substance may be higher fatty acid glyceride, lipoid, higher alkanol, higher fatty acid and its salt, an organic acid esterified compound, polysiloxane, fat-soluble vitamin, a silane coupling agent, a solid or semisolid alkane or its mixture, a linear alkyl compound and an amino acid. The higher fatty acid glyceride is selected from monoglyceride, diglyceride or triglyceride; the lipoid is preferably lecithin; the higher alkanol is selected from octacosanol and triacontanol: the higher fatty acid and its salt are selected from lauric acid, palmitic acid, stearic acid, magnesium stearate and octadecylamine; the organic acid esterified compound is selected from citrate, laurate and sucrose laurate; the polysiloxane is preferably silicone oil; the fat-soluble vitamin is selected from beta-carotenoid, vitamin E and vitamin A; the solid or semisolid alkane is selected from paraffin, microcrystalline wax and Vaseline; the linear alkyl compound is selected from sodium dodecyl sulfonate, sodium dodecyl sulfate, dodecyl dimethyl benzyl ammonium chloride and hexadecyl trimethyl ammonium chloride; and the amino acid is selected from leucine and alanine, The anionic surfactant layer includes a hydrophilic group and a hydrophobic tail chain, and the hydrophilic group is connected with the alkaline protector in a chemical adsorption manner. The hydrophilic group is a polar hydrophilic group, such as a carboxy group, a sulfuric acid group or a sulfonic acid group. The hydrophobic tailchain is a non-polar hydrophobic tail chain, including a hydrocarbon chain which includes at least 8 carbon atoms. The anionic surfactant may include a single hydrophilic group and a single hydrophobic tail chain, and it also may be an anionic Gemini surfactant formed by a dimer or an oligomer including the single hydrophilic group and the single hydrophobic tail chain. As an example, the anionic surfactant may be sodium dodecyl sulfate, sodium dodecyl sulfonate or sodium dodecyl benzene sulfonate.

After the implanted medical device according to the present application is implanted into a human body, for example, the absorbable lumen stent is implanted into a blood vessel, carboxylic acid produced by the degradation of the degradable polymer is distributed near the implanted device, and if a drug is loaded, it is released in the degradation process. At the moment, on one hand, the alkaline protector plays a spacer role for isolating the substrate covered thereby from an implantation environment to avoid contact between an acidic product of the degradable polymer and the iron alloy substrate, and on the other hand, hydroxide ions may be ionized from the alkaline substance of the alkaline protector or the alkaline substance may react with the hydrogen ions in a physiological environment, thereby generating a neutralization reaction with the acidic product to protect the iron substrate from not being corroded or being corroded slowly. All cations (such as $Na^+$, $K^+$, $Mg^{2+}$, $Zn^{2+}$ and $Ga^{2+}$) and anions (such as $CO_3^{2-}$ and $PO_4^{3-}$) which are left in the neutralization reaction are substances existing in the human body, so that no biocompatibility risk is caused.

With continuous consumption of the alkaline protector, the iron alloy substrate is exposed gradually, and the micro acidic environment which is not completely neutralized would accelerate corrosion of the iron-based alloy substrate. In other words, the iron alloy substrate is basically not corroded within a time period from the early stage of implantation of the device to complete consumption of the alkaline protector. Compared with a device which does not include the alkaline protector, the device has the advantage that, due to the existence of the alkaline protector, the iron-based alloy substrate starts corrosion later or the early corrosion of the substrate is slowed down; after the alkaline protector is completely consumed, the iron-based alloy substrate may be quickly corroded in the acidic environment formed by the degradable polymer, thereby meeting the time requirement of the device for the whole corrosion cycle. For different implanted devices, their corrosion cycles, namely the length of time from implantation to complete corrosion of the iron alloy substrate, are adjusted by adjusting the type, the mass, the concentration and the thickness of the alkaline substance in combination with parameters of the degradable polymer, such as the type, the mass and the molecular weight.

In addition, the early corrosion-delayed iron-based alloy substrate has little impact on the supporting force of the device in the early stage of implantation, which guarantees the mechanical property of the device and properly decreases the size of the iron-based alloy substrate, thus reducing the quantity of metal corrosion products and facilitating absorption and clearing of the corrosion products.

In order to increase the adhesive force of the alkaline protector on the surface of the iron-based alloy substrate, the surface of the iron-based alloy substrate may be roughened, or a degradable polymer middle layer may be disposed between the iron-based alloy substrate and the alkaline protector. The degradation product of the degradable polymer is neutral, and the degradable polymer may be selected from at least one of cellulose, lignin, starch, chitin and polyethylene glycol.

A manufacturing method of an absorbable iron-based alloy implanted medical device of the present application includes the steps of: the surface of an iron-based alloy substrate is covered with an alkaline protector, and the iron-based alloy substrate and/or the alkaline protector is covered with a degradable polymer. The step that the surface of the iron-based alloy substrate is covered with the alkaline protector includes: the surface of the iron-based alloy substrate is coated with a solution/suspension of the alkaline substance via spray coating, dip coating, brush coating, 3D printing, electrostatic spinning and embedding and the like, and the surface is dried, thereby forming the alkaline protector on the surface of the iron-based alloy substrate. The volume percentage of an alkaline substance in the formed alkaline protector is 20 to 100 percent. The alkaline substance includes, but not limited to, sodium hydroxide, potassium hydroxide, magnesium hydroxide, zinc hydroxide, magnesium oxide, zinc oxide, sodium carbonate, sodium bicarbonate, potassium carbonate, potassium bicarbonate, calcium carbonate, sodium phosphate. sodium hydrogen phosphate, potassium phosphate, potassium hydrogen phosphate, calcium phosphate, calcium hydrogen phosphate, sodium pyrophosphate, trisodium monohydrogen diphosphate, potassium pyrophosphate, tripotassium monohydrogen diphosphate, calcium pyrophosphate, calcium hydrogen diphosphate, sodium polyphosphate, potassium polyphosphate, calcium polyphosphate, ammonium polyphosphate, hydroxyapatite, carbonated hydroxyapatite, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium, ethylene diamine tetraacetic acid tetrapotassium, ethylene diamine tetraacetic acid calcium, sodium ethoxide, potassium ethoxide, calcium ethoxide, urea and hexamine.

In a process of covering the iron-based alloy substrate and the alkaline protector with the degradable polymer, the degradable polymer and a drug may be first dissolved in an organic solvent (such as ethyl acetate and chloroform) to form a mixed solution, and then the whole surface or part of the surface of the alkaline protector-containing iron-based alloy substrate is coated with the mixed solution and is dried to form a film via spray coating, dip coating, brush coating and electrostatic spinning and the like, with spray coating being preferred.

The method of coverage of the degradable polymer is only used as an example, and any proper method familiar to a person skilled in the art may be adopted to cover the surface of the iron-based alloy substrate and/or the surface of the alkaline protector with the degradable polymer. The degradable polymer may be degradable polyester and/or degradable polyanhydride. The degradable polyester is selected from the group consisting of polylactic acid, polyglycolic acid, poly(ethylene succinate), poly(β-hydroxybutyrate), polycaprolactone, polyethylene glycol adipate, a polylactic acid-glycollic acid copolymer and a polyhydroxybutyrate-pentanoate copolymer, or is selected from the group consisting of a physical blend of at least two of the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer, or is selected from the group consisting of a copolymer formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer. The polyanhydride is selected from poly1,3-bis(p-carboxyphenoxy)propane-sebacic acid, poly(erucic acid dimer-sebacic acid) or poly(fumaric acid-sebacic acid). The degradable polyester is selected from the group consisting of polylactic acid, polyglycolic acid, poly(ethylene succinate), poly(β-hydroxybutyrate), polycaprolactone, polyethylene glycol adipate, a polylactic acid-glycollic acid copolymer and a polyhydroxybutyrate-pentanoate copolymer; or the degradable polymer includes a blend of the above degradable polyester and the above degradable polyanhydride, or is a degradable copolymer formed by copolymerizing monomers of the above degradable polyester and the above degradable polyanhydride.

Clinically, the diastolic pressure (low pressure) and the systolic pressure (high pressure) of a coronary vessel of a normal person are 60 to 120 mmHg, but the systolic pressure of a hypertension patient is up to 175 mmHg, namely 23.3 kPa. In the case of coronary artery spasm, the systolic pressure of the vessel is 400 mmHg, namely 55 kPa. A psychological stress state, a cold stimulation, a strenuous exercise, coronary atherosclerosis and a local stimulation to the coronary artery due to coronary angiogram as well as one-time heavy smoking or drinking may all induce coronary artery spasm. Thus, in order to provide an effective support for the coronary vessel, the stent should at least bear the systolic pressure of 23.3 kPa in case of pulsation of the coronary vessel, and should be equipped to bear the systolic pressure of 55 kPa in case of vasospasm.

The design target of the iron-based alloy stent provided by each embodiment as follows is to meet the following clinical requirements: from the date of implantation, within preset time (for example within 1 month, 2 months, 3 months or other time lengths shorter than 3 months), the iron-based alloy substrate is nearly not corroded; after being implanted, the iron-based alloy stent may provide effective support for 3 months; after 3 months of implantation, the radial supporting strength is higher than or equal to 55 kPa; and the corrosion cycle is longer than 6 months but shorter than or equal to 24 months.

The definition of the stent of the specification 30008 in each embodiment is as follows: after the stent is expanded under the action of a nominal expansion pressure of 8 atm, the nominal diameter is 3 mm, and the nominal length is 8 mm.

It should be noted that, in each embodiment as follows, a normal fluctuation of the performance of a stent product within a designed allowable range, individual differences between the animals, an insufficient density of designed sampling points, and a system error unavoidably introduced by the test methods, may lead to fluctuations of monitored non-corrosion time points, radial strength data and complete corrosion time points of the stent within a certain range in an actual test.

Embodiment I

In this embodiment, an absorbable iron-based stent is taken as an example for description. Under an ideal condition, the absorbable iron-based stent should maintain its effective radial support (the supporting force is higher than 55 Pa) within a 3-month vascular repair period, and would be corroded as quickly as possible after a vascular function is recovered. It is required that the degradation period is generally 6 to 24 months.

First, the iron-based alloy substrate is manufactured by nitriding pure iron, with its initial radial strength of 145 kPa and mass of 4.5 to 5 mg. Sodium hydroxide is fully dissolved in an ethanol solution to obtain a saturated ethanol solution of sodium hydroxide which is used as an alkaline solution for manufacturing an alkaline protector. The surfaces of multiple iron-based alloy substrates are coated with the saturated ethanol solution of the sodium hydroxide via spraying coating to make a sodium hydroxide coating cover the whole surface of each iron-based alloy substate. After spray coating, the iron-based alloy substrates are dried and weighed, and at this time, the sodium hydroxide coating is about 6 μm in thickness. The surfaces of the dried alkaline coatings are coated with a poly-dl-lactic acid-ethyl acetate solution with a molecular weight of 200,000 via spray coating, thus covering the surfaces of the sodium hydroxide coatings, and then are dried, thus obtaining polymer coatings which are about 8 μm in thickness. Therefore, multiple absorbable iron-based stents are manufactured. The absorbable iron-based stents manufactured in this embodiment are implanted into an abdominal aorta of a rabbit; after 3 months, one stent is taken out, and observation finds that the surface of the stent is corroded to a certain extent, and its radial supporting force is measured as 80 kPa; and after the stents are implanted for 12 months, observation finds that the residual absorbable iron-based stents are completely corroded.

The alkaline protectors are disposed between the iron-based alloy substrates and degradable polymer layers of the stents in the embodiment to isolate the iron-based alloy substrates from a tissue environment of a human body and isolate the iron-based alloy substrates from an acidic environment produced in a degradation process of degradable polymers, thereby avoiding early corrosion of the iron-based alloy substrates; therefore, after the stents are implanted for 3 months, their radial supporting forces are reduced from the original 145 kPa to 80 kPa, which meet a radial supporting force requirement during the early stage of implantation of the stents; and after the alkaline protectors are consumed through acid-alkali neutralization, the substrates may be quickly corroded in the acidic environment produced by the degradable polymers, thereby realizing a 12-month degradation period and meeting a corrosion recycle requirement.

Embodiment II

What is different from Embodiment I is that sodium hydroxide coatings of the multiple manufactured absorbable iron-based alloy stents are about 20 μm in thickness, and polylactic acid coatings are about 12 μm in thickness. After being implanted for 3 months, one stent is taken out, and its radial supporting force is measured as 100 kPa. After the stents are implanted for 9 months, observation finds that the residual absorbable iron-based stents are completely degraded. It can be known from comparison with Embodiment I that using the same iron-based alloy substrates, by increasing the thicknesses of alkaline protector and the thicknesses of degradable polymer layers simultaneously, the radial supporting forces of the stents implanted for 3 months are slightly higher than those in Embodiment I. The stents according to this embodiment meet requirements on both the radial supporting force during the early stage of implantation and the corrosion cycle.

Embodiment III

What is different from Embodiment II is that polylactic acid coatings of manufactured absorbable iron-based alloy stents are about 8 μm in thickness. After being implanted for 3 months, one stent is taken out, and its radial supporting force is measured as 120 kPa. After the stents are implanted for 24 months, observation finds that the residual absorbable iron-based stents are completely degraded. It can be known from comparison with Embodiment II that using the same iron-based alloy substrates and the same alkaline protectors, by decreasing the thicknesses of degradable polymer layers, the radial supporting forces of the stents implanted for 3 months may be slightly increased, but their corrosion cycles are correspondingly prolonged. The stents according to this embodiment meet requirements on both the radial supporting force during the early stage of implantation and the corrosion cycle.

Embodiment IV

The same iron-based alloy substrates in Embodiment III are adopted, and nano magnesia powder and polyethylene glycol are ultrasonically dispersed in an ethanol solution to obtain a mixed suspension; and part of the surfaces of the iron-based alloy substrates are coated with the suspension via spray coating to form alkaline protectors which are 20 μm in thickness, and the volume percentage of the magnesia is 60 percent. After the alkaline protectors are dried, their surfaces are coated with a poly-dl-lactic acid-ethyl acetate solution with a molecular weight of 200,000 by spray coating; and polylactic acid coatings, which are about 8 μm in thickness, completely cover the surfaces of magnesia coatings, and after the polylactic acid coatings are dried, absorbable iron-based alloy stents are manufactured. The absorbable iron-based alloy stents are implanted into an abdominal aorta of a rabbit; after 3 months, one stent is taken out, and its radial supporting force is measured as 80 kPa; and after the stents are implanted for 12 months, observation finds that the stents are completely corroded. The stents according to this embodiment meet requirements on both the radial supporting force during the early stage of implantation and the corrosion cycle.

In order to further describe the technical effects of the absorbable iron-based alloy implanted medical device provided by the present application, three contrasts are taken as examples.

Contrast I

Contrast I provides a nitriding iron-based bare stent (which does not include a degradable polymer and an alkaline protector) of a specification 30008, with its original radial strength of 145 kPa and mass of 4.5 to 5 mg. Such stents are implanted into an abdominal aorta of a rabbit; after 3 months, one stent is taken out, and a mass loss test shows that it is slightly corroded, and its radial supporting strength is measured as 140 kPa, which meets a 3-month mechanical property requirement during the early stage of implantation. Then after being implanted for 24 months, another stent is taken out, and the mass loss test shows that it is not completely corroded, which indicates that the corrosion cycle of the nitriding iron stent without the degradable polymer layer is too long.

Contrast II

Contrast II provides an absorbable iron-based stent, and its manufacturing method is as follows: the surface of a nitriding iron stent, which has the original radial strength of 145 kPa and the mass of 4.5 to 5 mg and is of the specification 30008, is coated with a poly-dl-lactic acid-ethyl acetate solution with a molecular weight of 200,000 by spray coating, and the solution completely covers the whole surface of the stent; and after the surface is dried, the absorbable iron-based alloy stent with a poly-dl-lactic acid coating which is about 12 μm in thickness is manufactured. Such stents are implanted into an abdominal aorta of a rabbit; after 2 months, one stent is taken out, and observation finds that the struts of the stent are severely corroded and most of the struts are broken; then after 3 months, another stent is taken out, its radial supporting strength is measured as 55 kPa; and after the stents are implanted for 6 months, observation finds that they are completely corroded, which indicates that the corrosion is too fast, and the stents may not meet an early mechanical property requirement.

Contrast III

Contrast III provides an absorbable iron-based stent, and its manufacturing method is as follows: the surface of a nitriding iron stent, which has the original radial strength of 175 kPa and the mass of 5.5 to 6 mg and is of the specification 30008, is coated with a poly-dl-lactic acid-ethyl acetate solution with a molecular weight of 200,000 by spray coating, and the solution completely covers the whole surface of the stent; and after the surface is dried, the absorbable iron-based alloy stent with a poly-dl-lactic acid coating which is about 8 μm in thickness is manufactured. Such stents are implanted into an abdominal aorta of a rabbit; after 1 month, one stent is taken out and observation finds that the struts of the stent are corroded to a certain extent; then after 3 months, another stent is taken out, and its radial supporting strength is measured as 80 kPa, which meets a 3-month mechanical property requirement in the early stage of implantation: and after the stents are implanted for 12 months, observation finds that they are completely corroded.

Comparison of Contrast III with Embodiment II shows that under a condition of identical degradable polymer layers, although the corrosion cycle is equivalent to that of Embodiment II, the initial radial strength of the substrate is increased from 145 kPa to 175 kPa, and correspondingly, the mass of the substrate is increased from 4.5 to 5 mg to 5.5 to 6 mg, thereby correspondingly increasing the amount of metals implanted into a human body and the amount of degradation products, and increasing a biological risk of implantation. According to Embodiment II of the present application, by disposing the alkaline protector between the iron-based alloy substrate and the degradable polymer, and reasonable regulation of the content and the thickness of an alkaline substance in the alkaline protector, the early corrosion of the iron-based alloy substrate can be delayed or inhibited, so that after being implanted for 3 months, the device may still keep the effective radial supporting force and also meet the requirement on the corrosion cycle.

In conclusion, in the present application, by disposing the alkaline protector on the iron-based alloy substrate of the absorbable iron-based alloy implanted medical device, on one hand, the acidic product produced by the degradation of the polymer may be neutralized; and on the other hand, the alkaline protector may be used as a spacer configured to isolate the iron-based alloy substrate from an implantation environment and isolate the iron-based alloy substrate from a micro acidic environment formed by the degradation of the polymer at the beginning of implantation to relieve and even inhibit the early corrosion of the iron-based alloy substrate, so that the device may meets the mechanical property requirement during the initial stage of implantation. With consumption of the alkaline protector by neutralization, the exposed iron-based alloy substrate still may be quickly corroded in the micro acidic environment formed by the degradation of the degradable polymer layer, thereby meeting the requirement on the corrosion cycle of the stent.

The invention claimed is:

1. An absorbable iron-based alloy stent, comprising an iron-based alloy substrate having a surface, an alkaline protector disposed on the surface of the iron-based alloy substrate and having a surface, and a degradable polymer disposed on the surface of the alkaline protector, and wherein the alkaline protector comprises at least one alkaline substance; and the alkaline substance is selected from the group consisting of sodium hydroxide, zinc hydroxide, zinc oxide, sodium carbonate, sodium bicarbonate, potassium carbonate, potassium bicarbonate, sodium phosphate, sodium hydrogen phosphate, potassium phosphate, potassium hydrogen phosphate, sodium pyrophosphate, trisodium monohydrogen diphosphate, potassium pyrophosphate, tripotassium monohydrogen diphosphate, sodium polyphosphate, potassium polyphosphate, ammonium polyphosphate, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium, ethylene diamine tetraacetic acid tetrapotassium, ethylene diamine tetraacetic acid calcium, sodium ethoxide, potassium ethoxide, calcium ethoxide, urea and hexamine; and
wherein the thickness of the alkaline protector is 6 μM, the thickness of the polymer is 8 μM, and the mass of the iron-based alloy substrate is 4.5-5 mg; or wherein the thickness of the alkaline protector is 20 μM, the thickness of the polymer is 12 μM, and the mass of the iron-based alloy substrate is 4.5-5 mg; or wherein the thickness of the alkaline protector is 20 μM, the thickness of the polymer is 8 μM, and the mass of the iron-based alloy substrate is 4.5-5 mg.

2. The absorbable iron-based alloy stent according to claim 1, wherein the alkaline protector covers the entire surface of the iron-based alloy substrate, and the degradable polymer covers at least part of the surface of the alkaline protector.

3. The absorbable iron-based alloy implanted stent according to claim 1, wherein the alkaline protector covers part of the surface of the iron-based alloy substrate, and the degradable polymer covers at least part of the surface of the alkaline protector and/or at least part of the surface of a region, which is not covered by the alkaline protector, in the iron-based alloy substrate.

4. The absorbable iron-based alloy stent according to claim 1, wherein the alkaline protector comprises a weak acid and strong alkali salt which is selected from the group consisting of sodium pyrophosphate, trisodium monohydrogen diphosphate, potassium pyrophosphate, tripotassium monohydrogen diphosphate, sodium polyphosphate, potassium polyphosphate, ammonium polyphosphate, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium and ethylene diamine tetraacetic acid tetrapotassium.

5. The absorbable iron-based alloy stent according to claim 1, wherein the iron-based alloy substrate is pure iron or an iron-based alloy with a carbon content less than or equal to 2.11 wt. %.

6. The absorbable iron-based alloy stent according to claim 1, wherein the degradable polymer is selected from degradable polyester and/or degradable polyanhydride; the degradable polyester is selected from the group consisting of polylactic acid, poly(lactic acid-glycolic acid), polycaprolactone, polyhydroxyalkanoate, polyacrylate, poly(ethylene succinate), poly(β-hydroxybutyrate) and polyethylene glycol adipate, or is selected from the group consisting of a physical blend of at least two of the polylactic acid, the polyglycolic acid, the poly(ethylene succinate), the poly(β-hydroxybutyrate), the polycaprolactone, the polyethylene glycol adipate, a polylactic acid-glycollic acid copolymer and a polyhydroxybutyrate-pentanoate copolymer, or is selected from the group consisting of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer; and the degradable polyanhydride is selected from the group consisting of poly1,3-bis(p-carboxyphenoxy) propane-sebacic acid, poly(erucic acid dimer-sebacic acid) or poly(fumaric acid-sebacic acid), or the degradable polymer is a copolymer formed by copolymerizing at least two of monomers forming the degradable polyester and the degradable polyanhydride.

7. An absorbable iron-based alloy stent, comprising an iron-based alloy substrate having a surface, an alkaline protector disposed on the surface of the iron-based alloy substrate and having a surface, and a degradable polymer disposed on the surface of the alkaline protector, and wherein the alkaline protector comprises at least one alkaline substance; and the alkaline substance is selected from the group consisting of sodium hydroxide, zinc hydroxide, sodium carbonate, sodium bicarbonate, potassium carbonate, potassium bicarbonate, sodium phosphate, sodium hydrogen phosphate, potassium phosphate, potassium hydrogen phosphate, sodium pyrophosphate, trisodium monohydrogen diphosphate, potassium pyrophosphate, tripotassium monohydrogen diphosphate, sodium polyphosphate, potassium polyphosphate, ammonium polyphosphate, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium, ethylene diamine tetraacetic acid tetrapotassium, ethylene diamine tetraacetic acid calcium, sodium ethoxide, potassium ethoxide, calcium ethoxide, urea and hexamine;

wherein the alkaline protector further comprises a slow release assisted substance for prolonging the release time of the alkaline substance; the slow release assisted substance comprises a thickener; the thickener is mixed with the at least one alkaline substance to form a mixture; and the volume percentage of the alkaline substance in the mixture is greater than or equal to 20 percent but less than 100 percent; and wherein the thickness of the alkaline protector is 6 μM, the thickness of the polymer is 8 μM, and the mass of the iron-based alloy substrate is 4.5-5 mg; or wherein the thickness of the alkaline protector is 20 μM, the thickness of the polymer is 12 μM, and the mass of the iron-based alloy substrate is 4.5-5 mg; or wherein the thickness of the alkaline protector is 20 μM, the thickness of the polymer is 8 μM, and the mass of the iron-based alloy substrate is 4.5-5 mg.

8. The absorbable iron-based alloy stent according to claim 7, wherein the alkaline protector covers the entire surface of the iron-based alloy substrate, and the degradable polymer covers at least part of the surface of the alkaline protector.

9. The absorbable iron-based alloy implanted stent according to claim 7, wherein the alkaline protector covers part of the surface of the iron-based alloy substrate, and the degradable polymer covers at least part of the surface of the alkaline protector and/or at least part of the surface of a region, which is not covered by the alkaline protector, in the iron-based alloy substrate.

10. The absorbable iron-based alloy stent according to claim 7, wherein the alkaline protector comprises a weak acid and strong alkali salt which is selected from the group consisting of sodium pyrophosphate, trisodium monohydrogen diphosphate, potassium pyrophosphate, tripotassium monohydrogen diphosphate, sodium polyphosphate, potassium polyphosphate, ammonium polyphosphate, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium and ethylene diamine tetraacetic acid tetrapotassium.

11. The absorbable iron-based alloy stent according to claim 7, wherein the iron-based alloy substrate is pure iron or an iron-based alloy with a carbon content less than or equal to 2.11 wt. %.

12. The absorbable iron-based alloy stent according to claim 7, wherein the degradable polymer is selected from degradable polyester and/or degradable polyanhydride; the degradable polyester is selected from the group consisting of polylactic acid, poly(lactic acid-glycolic acid), polycaprolactone, polyhydroxyalkanoate, polyacrylate, poly(ethylene succinate), poly(β-hydroxybutyrate) and polyethylene glycol adipate, or is selected from the group consisting of a physical blend of at least two of the polylactic acid, the polyglycolic acid, the poly(ethylene succinate), the poly(β-hydroxybutyrate), the polycaprolactone, the polyethylene glycol adipate, a polylactic acid-glycollic acid copolymer and a polyhydroxybutyrate-pentanoate copolymer, or is selected from the group consisting of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer; and the degradable polyanhydride is selected from the group consisting of poly1,3-bis(p-carboxyphenoxy) propane-sebacic acid, poly(erucic acid dimer-sebacic acid) or poly(fumaric acid-sebacic acid), or the degradable polymer is a copolymer formed by copolymerizing at least two of monomers forming the degradable polyester and the degradable polyanhydride.

13. An absorbable iron-based alloy stent, comprising an iron-based alloy substrate having a surface, an alkaline protector disposed on the surface of the iron-based alloy substrate and having a surface, and a degradable polymer disposed on the surface of the alkaline protector, and wherein the alkaline protector comprises at least a weak acid and strong alkali salt; and the weak acid and strong alkali salt is selected from the group consisting of sodium pyrophosphate, trisodium monohydrogen diphosphate, potassium pyrophosphate, tripotassium monohydrogen diphosphate, sodium polyphosphate, potassium polyphosphate, ammonium polyphosphate, sodium borate, potassium borate, calcium borate, sodium oxalate, potassium oxalate, calcium oxalate, trisodium citrate, sodium dihydrogen citrate, tripotassium citrate, potassium dihydrogen citrate, calcium citrate, calcium hydrogen citrate, sodium tartrate, potassium tartrate, calcium tartrate, ethylene diamine tetraacetic acid tetrasodium and ethylene diamine tetraacetic acid tetrapotassium; and wherein the thickness of the alkaline protector is 6 μM, the thickness of the polymer is 8 μM, and the mass of the iron-based alloy substrate is 4.5-5 mg; or wherein the thickness of the alkaline protector is 20 μM, the thickness of the polymer is 12 μM, and the mass of the iron-based alloy substrate is 4.5-5 mg; or wherein the thickness of the alkaline protector is 20 μM, the thickness of the polymer is 8 μM, and the mass of the iron-based alloy substrate is 4.5-5 mg.

14. The absorbable iron-based alloy stent according to claim 13, wherein the alkaline protector further comprises a slow release assisted substance for prolonging the release time of the alkaline substance; the slow release assisted substance comprises a thickener; the thickener is mixed with the at least one alkaline substance to form a mixture; and the volume percentage of the alkaline substance in the mixture is greater than or equal to 20 percent but less than 100 percent.

\* \* \* \* \*